United States Patent [19]

Jenko et al.

[11] 4,200,761
[45] Apr. 29, 1980

[54] PROCESS FOR PREPARING N-CYANO-N'METHYL-N''-{2-[(4-METHYL-5-IMIDAZOLYL)-METHYLTHIO]-ETHYL} GUANIDINE

[75] Inventors: Branko Jenko, Ljubljana-Polje; Igor Langof; Jōza Habjan, both of Ljubljana, all of Yugoslavia

[73] Assignee: LEK, tovarna farmacevtskih in kemicnih izdelkov, n.sol.o., Ljubljana, Yugoslavia

[21] Appl. No.: 31,239

[22] Filed: Apr. 18, 1979

[30] Foreign Application Priority Data

Apr. 26, 1978 [YU] Yugoslavia .............................. 998/78

[51] Int. Cl.² .......................................... C07D 233/64
[52] U.S. Cl. .................................................... 548/342
[58] Field of Search ........................................ 548/342

[56] References Cited

U.S. PATENT DOCUMENTS

| | | | |
|---|---|---|---|
| 3,876,647 | 4/1975 | Durant et al. | 546/306 |
| 3,897,444 | 7/1975 | Durant et al. | 548/342 |
| 3,950,333 | 4/1976 | Durant et al. | 548/342 |
| 4,013,678 | 3/1977 | Brown et al. | 548/342 |
| 4,025,527 | 5/1977 | Durant et al. | 548/342 |
| 4,049,671 | 9/1977 | Durant et al. | 548/342 |
| 4,112,234 | 9/1978 | Crenshaw et al. | 548/342 |

FOREIGN PATENT DOCUMENTS 2344779  3/1974  Fed. Rep. of Germany ........... 548/342

*Primary Examiner*—Natalie Trousof
*Attorney, Agent, or Firm*—Pollock, Vande Sande and Priddy

[57] ABSTRACT

A process of preparing

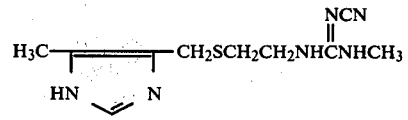

by reacting 4-thiomethyl-5-methyl imidazole with N-cyano-N'-methyl-N''-(2-chloroethyl) guanidine in a two-phase system under the conditions of phase transfer catalysis.

10 Claims, No Drawings

PROCESS FOR PREPARING N-CYANO-N'METHYL-N''-{2-[(4-METHYL-5-IMIDAZOLYL)-METHYLTHIO]-ETHYL} GUANIDINE

The invention relates to a new process for preparing N-cyano-N'-methyl-N''-{2[(4-methyl-5-imidazolyl)-methylthio]-ethyl}guanidine of the formula

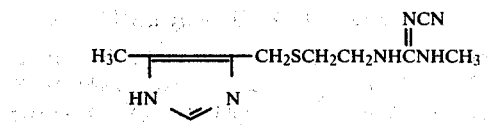

The compound is known to be pharmacologically active as an extraordinarily efficient antagonist of hystamine on $H_2$ receptors. It has a hindering effect upon basal as well as stimulated secretion of gastric acid and pepsin.

N-cyano-N'-methyl-N''-{2-[(4-methyl-5-imidazolyl)-methylthio]-ethyl}guanidine is an already known compound. For the first time it was disclosed in the British Pat. No. 1 338 169.

Several processes for preparing the compound were disclosed in the German Offenlegungsschrift 2 344 779 by the same inventors.

The prior art processes (German Offenlegungsschrift No. 2 334 779) are based on the reaction of 4-halomethyl-, 4-hydroxymethyl- or 4-methoxymethyl-5-methyl imidazole or its hydrochloride or hydrobromide with cysteamine. The reaction results in the formation of the intermediate compound 4-[(2-aminoethyl)thiomethyl]-5methyl imidazole, which is reacted with methylisothiocyanate to form N-methyl-N'-{2-[(4-imidazolyl5-methyl)-methylthio]-ethyl}-thiourea, which is then reacted with lead cyanamide to form the final compound of the formula I.

Furthermore, the final compound I can be obtained by reacting 4-[(2-aminoethyl)-thiomethyl]-5-methyl imidazole with N-cyano-N',S-dimethylisothiourea or with dimethylcyanodithioimido carbonate to form N-cyano-N'-{2-[(5-methylimidazole-4-yl)-methylthio]-ethyl}-S-methylisothiourea, which reacts with methylamine, thus yielding the final compound I.

The first step in the process disclosed in the German Offenlegungsschrift No. 2 344 779 includes heating a solution of 4-methyl-5-[(2-aminoethyl)-thiomethyl)]imidazole and N-cyano-N', S-dimethylisothiourea in acetonitrile for 24 hours under reflux. After the evaporation of the solvent and purification by chromatography on silicagel, using acetonitrile as eluent, there is isolated the crude product, which is recrystallized from a mixture of acetonitrile/ether.

In a further synthesis described in the above-mentioned German Offenlegungsschrift No. 2 344 779, N-methyl-N'-{2-[(4-methyl-5-imidazolyl)-thiomethyl]-ethyl}-thiourea is reacted in acetonitrile with lead cyanamide. After addition of dimethylformamide and heating for 24 hours under reflux with constant stirring, there is obtained the compound I.

In this synthesis, too, purification by chromatography on silicagel and recrystallization are necessary.

The third process described is carried out starting with 4-methyl-5-[(2-aminoethyl)-thiomethyl] imidazole and adding an ethanolic solution of dimethyl-cyanodithioimidocarbonate with stirring at room temperature. After evaporation of the solvent and digestion in water, it is necessary to recrystallize the intermediate N-cyano-N'-{2-[(4-methyl-5-imidazolyl)-thiomethyl]-ethyl}-S-methyl-isothiourea two more times from a mixture of isopropanol/ether. To the ethanolic solution of the pure intermediate, there is added an ethanolic solution of methylamine and the reaction mixture is allowed to stand at room temperature. After evaporating the solvent, two recrystallizations of the final compound I from a mixture of isopropanol/petroleum ether are necessary to obtain the pure product.

There is also described a process without intermediary isolation of N-cyano-N'-{2-[(4-methyl-5-imidazolyl)-thiomethyl]-ethyl}-S-methyl-isothiourea.

All described processes have in common that they are carried out in two or more steps, starting from 4-hydroxymethyl-, 4-halomethyl- or 4-methoxymethyl-5-methylimidazole.

Substantial losses and hence poor yields of about 60% occur during the isolation, purification and recrystallization of the intermediates and of the final product.

When using the described processes, great difficulties arise particularly on an industrial scale, due to the numerous recrystallizations and purifications of the products by chromatography.

The aim of the present invention is to provide a process for preparing N-cyano-N'-methyl-N''-{2-[(4-methyl-5-imidazolyl)-methylthio]-ethyl}guanidine with high yields and short reaction times. The final product should be obtained easily and with high purity without necessity of complicated and time consuming methods of chromatographical purification.

This aim is attained by reacting 4-thiomethyl-5-methyl imidazole with N-cyano-N'-methyl-N''-(2-chloroethyl)guanidine in a single step in a two-phase system under the conditions of phase transfer catalysis using quaternary ammonium or quaternary phosphonium salts, e.g. methyl tricaprylylammonium chloride, benzyltriethylammonium chloride, benzyltriphenylphosphonium chloride, hexadecyltributylphosphonium bromide, as catalysts. The reaction may be carried out at a temperature of 0° to 50° C., preferably at room temperature, and may also be carried out in the presence of a strong base such as sodium hydroxide.

Another advantage of the process according to the invention is the fact that after the evaporation of the solvent, the final product is obtained with such a purity that a single crystallization from isopropanol or from a mixture of isopropanol and ether is sufficient. The yields of the final compound N-cyano-N'-methyl-N''-{2-[(4-methyl-5-imidazolyl)-methylthio]-ethyl}guanidine are exceptionally high and range between 85 and 90% of the theoretical yield. A further advantage of the present process over the prior art processes for the synthesis of N-cyano-N'-methyl-N''-{2-[(4-methyl-5-imidazolyl)-methylthio]-ethyl}guanidine resides in the fact that in the process according to the invention the use of cysteamine-hydrochloride can be avoided. This expensive chemical is replaced by 2-chloro-ethyl-amine, a cheaper and readily availbale compound.

Surprisingly, it was found that the starting substances, 4-thiomethyl-5-methyl imidazole and N-cyano-N'-methyl-N''-(2-chloroethyl) guanidine had been disclosed neither in the above-cited patents nor in any other literature source and, consequently, they represent novel compounds.

5-methyl-4-thiomethyl-imidazole hydrochloride can be prepared either by reacting 5-methyl-4-chloromethyl imidazole with KSH in the presence of polyethyleneglycol-dimethylether as phase transfer catalyst or by reacting 5-methyl-4-chloromethylimidazole hydrochloride with thiourea and converting the intermediate compound S-(4-methyl-5-methylimidazolyl)-isothiourea with potassium carbonate into the desired product.

N-cyano-N'-methyl-N''-(2-chloroethyl)guanidine can be prepared by reacting 2-chloroethylamine with dimethylcyanoimidodithio-carbonate in ethanolic solution and converting the intermediarily formed N-cyano-N'-(2-chloroethyl)-S-methyl-isothiourea with methylamine to the desired product.

The invention will be illustrated by the following non-limitative Examples.

EXAMPLE 1

N-cyano-N'-methyl-N''-{2-[(4-methyl-5-imidazolyl)-methylthio]-ethyl}guanidine 5-methyl-4-thiomethyl-imidazole hydrochloride (16.5 g, 0.1 mole) was dissolved in methanol (200 ml). 50% aqueous solution of NaOH (20 ml) and the catalyst tricaprylylmethylammonium chloride (Aliquat 336) (2.5 g, 0.006 mole) were added, followed by the dropwise addition of N-cyano-N'-methyl-N''-(1-chloroethyl)-guanidine (16.0 g, 0.1 mole) in methanol (100 ml), and the reaction mixture was stirred for 2.5 hours at room temperature. The reaction mixture was evaporated to dryness, isopropanol (120 ml) was added thereto, the inorganic salts were filtered off. The filtrate was evaporated to dryness, the residue recrystallized from isopropanol, yielding the desired compound (22.7 g, 90.0%), m.p. 140°–142° C.

EXAMPLE 2

N-cyano-N'-methyl-N''-{2-[(4-methyl-5-imidazolyl)-methylthio]-ethyl}guanidine 4-thiomethyl-5-methylimidazole (12.8 g, 0.1 mole) was suspended in acetonitrile (250 ml). Sodium hydroxyde (50% aqueous solution, 15 ml) and the catalyst triethylbenzylammonium chloride (TEBA) (1.16 g) were added thereto, followed by dropwise addition of N-cyano-N'-methyl-N''-(2-chloroethyl)guanidine (16.0 g, 0.1 mole) within 0.5 hours. The reaction mixture was stirred for 5 hours at room temperature. The solvent was evaporated in vacuo. Water (150 ml) and tert. butanol (100 ml) were added to the reaction residue. The phases were separated. The aqueous phase was re-extracted with tert. butanol (100 ml), the organic phase was dried and evaporated to dryness. The crude product was recrystallized from a mixture of isopropanol/ether, yielding pure N-cyano-N'-methyl-N''-{2-[(4-methyl-5-imidazolyl)-methylthio]-ethyl}guanidine (22.7 g, 90%), m.p. 141°–142° C.

EXAMPLE 3

N-cyano-N'-methyl-N''-{2-[(4-methyl-5-imidazolyl)-methylthio]-ethyl}guanidine 5-methyl-4-thiomethyl-imidazole hydrochloride (8.2 g, 0.05 mole) was dissolved in ethanol (100 ml). Hexadecyltributylphosphonium chloride C₁₆H₃₃P(+)(C₄H₉)₃Cl(−)(1.16 g, 0.0025 mole) and sodium hydroxyde (50% aqueous solution, 10 ml) were added and the mixture was stirred for 20 minutes at room temperature. N-cyano-N'-methyl-N''-(2-chloroethyl) guanidine (8.5 g, 0.05 mole) in ethanol (60 ml) was added dropwise within 15 minutes and the mixture was stirred for two more hours at room temperature and then evaporated to dryness. Isopropanol (100 ml) was added to the residue, the inorganic salts were filtered off, the filtrate was evaporated to dryness and the crude residue was recrystallized from acetonitrile, yielding the desired compound (11.1 g, 88%), m.p. 141°–143° C.

Preparation of the starting materials

EXAMPLE 4

5-methyl-4-thiomethyl-imidazole hydrochloride

Polyethylene glycol dimethylether (4.0 g, 0.01 mole, average M.W. 400) and KSH (7.2 g, 0.01 mole) were added to the solution of 5-methyl-4-chloromethyl-imidazole (13.0 g, 0.1 mole) in ethanol (150 ml). The mixture was stirred for 1 hour at 20° C., KCl was filtered off and hydrogen chloride was passed into the filtrate to reach the pH of 1. The solution was evaporated to dryness and the residue was recrystallized from isopropanol yielding the desired compound (14.9 g, 90.5%), m.p. 282°–285° C.

EXAMPLE 5

5-methyl-4-thiomethyl-imidazole hydrochloride 5-methyl-4-chloromethyl-imidazole hydrochloride (1.70 g, 0.1 mole) and thiourea (0.84 g, 0.11 mole) were refluxed for 6 hours in acetone (200 ml), giving S-(4-methyl-5-methylimidazolyl)-isothiourea. The solvent was evaporated and a saturated aqueous solution of potassium carbonate (50 ml) was added to the residue. After stirring for 30 minutes at 70° C. and evaporating the water, isopropanol (100 ml) was added and hydrogen chloride was passed into the solution to reach the pH of 1. The inorganic salts was filtered off and the filtrate was evaporated to dryness. Recrystallization from isopropanol yielded the desired compound (1.45 g, 86.8%), m.p. 283°–285° C.

EXAMPLE 6

N-cyano-N'-methyl-N''-(2-chloroethyl)guanidine 2-chloro-ethylamine (8.0 g, 0.1 mole) was dissolved in ethanol (50 ml). A solution of dimethylcyanimidodithio-carbonate (14.6 g, 0.1 mole) in ethanol (120 ml) was added dropwise to the above solution. The reaction mixture was heated for 2 hours at reflux temperature and allowed to cool to the room temperature. A 33% ethanolic solution of methylamine (110 ml) was added and the mixture was heated for 30 minutes at 50° C. The reaction mixture was evaporated to dryness to yield the desired compound (15.3 g, 90%) as an oil. Rf=0.15 (mobile phase chloroform/methanol 8:2).

What is claimed is:

1. A process for preparing N-cyano-N'-methyl-N''-{2-[(4-methyl-5-imidazolyl)-methylthio]-ethyl}guanidine of the formula

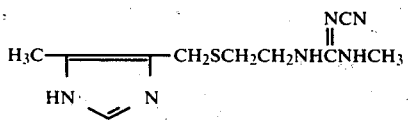

characterized in that 4-thiomethyl-5-methyl imidazole is reacted with N-cyano-N'-methyl-N''-(2-chloroethyl)-guanidine in a two-phase system under the conditions of phase transfer catalysis.

2. A process according to claim 1, characterized in that quaternary ammonium salts or quaternary phosphonium salts are used as phase transfer catalysts.

3. A process according to claim 1, characterized in that the reaction is carried out in a two-phase system at a temperature of 0° to 50° C.

4. A process according to claim 1, characterized in that the reaction is carried out in the presence of a strong base.

5. The process of claim 2 wherein said salts are selected from the group of methyltricaprylylammonium chloride, hexadecyltributylphosphonium bromide, benzyltriethylammonium chloride or benzyltriphenylphosphonium chloride.

6. A process according to claim 1, characterized in that the reaction is carried out in a two-phase system at room temperature.

7. A process according to claim 1, characterized in that the reaction is carried out in the presence of sodium hydroxide.

8. The process of claim 2 characterized in that the reaction is carried out in a two-phase system at a temperature of 0° to 50° C. and in the presence of a strong base.

9. The process of claim 5 characterized in that the reaction is carried out in a two-phase system at a temperature of 0° to 50° C. and in the presence of a strong base.

10. The process of claim 5 characterized in that the reaction is carried out in a two-phase system at room temperature and in the presence of sodium hydroxide.

* * * * *